Figure 3:
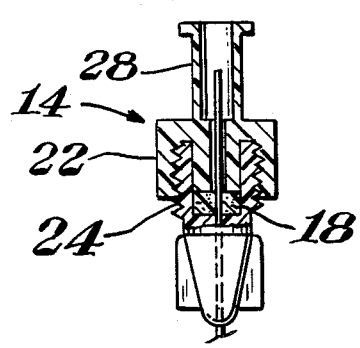

United States Patent [19]

Bommarito

[11] Patent Number: 4,894,056
[45] Date of Patent: Jan. 16, 1990

[54] METHOD AND APPARATUS FOR CLEARING OCCLUDED LUMENS OF ENTERAL FEEDING TUBES

[76] Inventor: Alexander A. Bommarito, 12555 W. Freeland Rd., Freeland, Mich. 48623

[21] Appl. No.: 163,749

[22] Filed: Mar. 3, 1988

Related U.S. Application Data

[63] Continuation-in-part of Ser. No. 56,453, Jun. 1, 1987, abandoned.

[51] Int. Cl.[4] .............................................. A61M 5/00
[52] U.S. Cl. .................................... 604/267; 604/159
[58] Field of Search .............. 604/164, 170, 171, 158, 604/159, 163, 267

[56] References Cited

U.S. PATENT DOCUMENTS

| | | | |
|---|---|---|---|
| 878,199 | 2/1908 | Freeman | 604/267 |
| 3,416,532 | 12/1968 | Grossman | 604/267 |
| 3,863,641 | 2/1975 | Popa | 604/267 |
| 4,159,022 | 6/1979 | Peusner | 604/159 |
| 4,228,802 | 10/1980 | Trott | 604/267 |
| 4,419,094 | 12/1983 | Patel | 604/158 |
| 4,613,329 | 9/1986 | Bodicky | 604/158 |
| 4,615,472 | 10/1986 | Nash | 604/159 |
| 4,767,409 | 8/1988 | Brooks | 604/163 |

OTHER PUBLICATIONS

Caos and Gogel, "A Simple Method for Clearing Obstructed Enteral Feeding Tubes", *Gastrointestinal Endoscopy*, vol. 32, No. 1, p. 55, 1986.

*Primary Examiner*—Stephen C. Pellegrino
*Assistant Examiner*—Ralph Lewis
*Attorney, Agent, or Firm*—Merlin B. Davey

[57] ABSTRACT

This invention provides a method and device for restoring the patency of feeding tubes by removal of feedings that are blocking the lumen of the tubes. The device provides a means of contacting the occlusions with solubilizing agents and employs fluid erosion techniques and mechanical force and provides for the restoration of the therapeutic plan without the major complications and cost of replacing tubes already in place.

1 Claim, 1 Drawing Sheet

U.S. Patent      Jan. 16, 1990      4,894,056

METHOD AND APPARATUS FOR CLEARING OCCLUDED LUMENS OF ENTERAL FEEDING TUBES

CROSS-REFERENCE TO RELATED APPLICATION

This application is a continuation-in-part of application Ser. No. 056,453 filed June 1, 1987, now abandoned.

BACKGROUND OF THE INVENTION

Many acutely and chronically ill patients, who are severely malnourished and in negative nitrogen balance, have no desire to eat or are unable to eat spontaneously. Proper nutrition plays a crucial role in the therapy of multiple trauma, cancer, or neurologically impaired patients. Central and enteral hyperalimentation are excellent methods of treating nutritional deficiencies.

Total health care is contingent upon sound nutritional status. Practicing physicians and physician extenders evaluating the clinical and nutritional status of their patients should be able to implement an effective central or enteral feeding program when needed. The wide range of nutritional preparations and feeding tubes available makes it possible to meet the differing requirements of varying pathological states, either accompanying or causing malnutrition.

The enteral route is a primary means of improving nutritional status simply, economically, and with good toleration in most patients. Several options are available when selecting a tube for enteral feedings. The standard nasogastric tube is made of polyvinyl chloride. One of its distinct advantages is that it may already be in place as part of the ongoing therapeutic plan. Its large bore allows for easy aspiration of gastric contents and the tube is less likely to occlude from medications and feedings.

The main disadvantage of polyvinyl chloride tubing is that the plasticizer, needed to keep the tubing flexible and soft, leaches out and the resulting rigidity can lead to irritation of the pharynx and esophagus. Erosions of the nasal septum, alar rim, and esophagus can develop during prolonged utilization, leading to significant complications and risk. In addition, the inability to place this tube beyond the pylorus increases the risk of gastric retention and regurgitation. Poor patient tolerance due to tube irritation and rigidity and the lack of ready postpyloric placement are undesirable properties inherent in the polyvinyl chloride tubes.

Alternatives to the polyvinyl chloride tubes are the silastic or polyurethane tubes such as the Dobbhoff®, Entriflex®, Keofeed®, Vivonex® and Ross tubes. The persistently soft, pliable, less erosive characteristics of these tubes provide greater patient comfort and are extremely well tolerated for prolonged periods of time. Weighted, encapsulated mercury or tungsten tips aid in passage through the pylorus, and in this regard, the Dobbhoff tube is favored for its larger and heavier tip. Since this silastic tube is longer than the nasogastric tube and encapsulates a weighted tip, migration into the duodenum is readily accomplished, providing a diminished risk of pulmonary aspiration. Patients with anorexia or nausea are able to tolerate this tube well, and even if vomiting occurs, the heavier weighted Dobbhoff will usually remain in place.

Disadvantages of the silastic tube lie mainly in its small lumen. Medications and feedings cause frequent occlusions in patients even with irrigation and well crushed or liquid state medications. Aspiration of gastric or intestinal contents through these small tubes to determine accuracy of position is usually unsatisfactory and x-rays must often be ordered. These tubes are more difficult to pass, but are the standard used in enteral feeding today. A number of deaths have been reported over the last three years due to stilets used to stiffen the tube for easier placement. The other serious complication associated with tube feedings is the unrecognized placement of the tube outside the gastrointestinal tract, i.e., trachea, bronchus, pleural cavity, mediastinum, or abdominal cavity. Infusion of solutions into these areas can lead to sepsis, abscess formation, and mortality.

It is standard practice to use small lumen tubes and to pull and replace tubes if occlusions occur. This has the added cost of x-rays, new feeding tubes, nursing time, lost feeding time and additional hospitalization in many cases, in addition to the above-mentioned risks and/or complications.

The failure of the hitherto employed means to clear occluded feeding tubes is related to the inability of solubilizing agents to reach the material blocking the lumen of the tube. Water will solubilize most materials blocking the lumen, but attempts to irrigate the tube are fruitless and the risk of breaking the tube with water pressure is high. So the tubes are pulled and replaced, resulting in accompanying complications and costs.

One method of attempting to solve this problem has been reported recently in Vol. 32, No. 1, 1986 (pg. 55) of Gastrointestinal Endoscopy wherein Caos and Gogel employed a standard cytology brush (Olympus BC-1J) for clearing a Dobbhoff enteric feeding tube (8 FR/109 cm). While reporting success with straight tubes, with multiply looped tubes and with extreme fixed angles, this procedure has the disadvantage of failing when tubes are kinked or when the occlusions are hard. At such times, tube perforation can occur and this procedure has not become acceptable practice due to the inherent risk of tube perforation.

SUMMARY OF THE INVENTION

This invention provides a procedure and apparatus for clearing and cleaning the occluded lumens of enteral feeding tubes used in administration of foods. These tubes often become occluded by foods with which they are in contact or which are delivered through them.

The apparatus of this invention comprises a polycarbonate tube having a first end and a second end and being adapted to be inserted in an enteral feeding tube, said first end being shaped for permitting high fluid flow resulting in dislodging occluded material when rotated thereagainst and said second end being adapted for connection to a liquid injection means.

The polycarbonate tube employed in the apparatus of this invention has been found to have the necessary strength and flow characteristics which permit it to be inserted into an enteral feeding tube which is generally positioned in a curved path in body cavities with essentially no likelihood of causing perforations in the enteral tube thereby providing the necessary safety factor for the patient. Because of these properties the apparatus of this invention has been found to provide timely and inexpensive removal of occlusions in enteral feeding tubes to the delight of both patients and doctors.

The method of this invention comprises a method of removing occlusions from tubes employed for feeding which comprises inserting an inner polycarbonate tube into said occluded tube such that a first end is positioned adjacent to the occlusion and passing warm water or an enzyme solution through said inner tube while providing a rotary and/or oscillatory motion to said inner polycarbonate tube.

The pressure needed to remove an occlusion from an obstructed feeding tube or catheter will vary with the size of the inner tube. For example, an 18 gauge tube may require between 20 and 30 psi for the removal of an obstruction. Pressures up to 40 psi may be employed without harming a blocked tube. A flow of 15 cc. per minute of warm water can be achieved at a pressure of 30 psi employing an 18 gauge tube.

Figure 2:
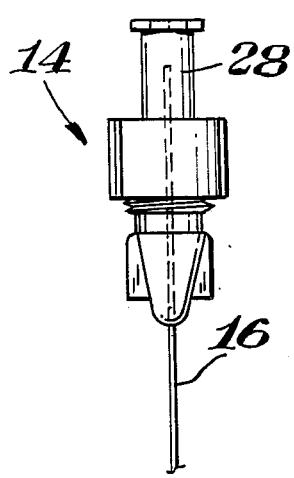
Figure 2:
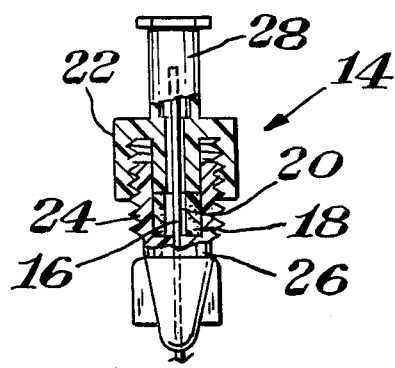
Figure 1:
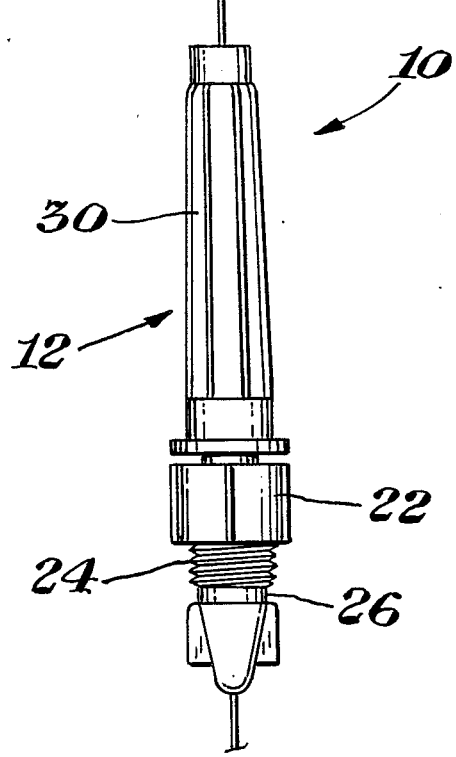

The invention is further illustrated by the accompanying drawings wherein:

FIG. 1 is a side view of the apparatus of the invention;

FIG. 2 is a sectional view of syringe adaptor 14 showing the means for controlling movement of tube 16 in the open or slidable position; and FIG. 3 is a sectional view of syringe adaptor 14 showing the means for controlling movement of tube 16 in the closed or locked position.

Referring to FIG. 1, the Introreducer® 10, of this invention comprises a pressure distributor adaptor 12 and a syringe adaptor 14, within each of which a polycarbonate tube 16 is positioned. In syringe adaptor 14, tube 16 is normally fixedly positioned while in pressure distributor adaptor 12, tube 16 is alternately fixedly or slidably positioned. Handle 30, of pressure distributor adaptor 12, serves as a force distributor or means to prevent kinking of tube 16 as pressure is applied to dislodge the occlusion. Handle 30 is generally about 2 to 4 inches in length. Polycarbonate tube 16 advantageously has an outside diameter of from 0.025 to 0.060 inches and is preferably about 0.040 inches outside diameter with an inner lumen of from 0.010 to 0.030 inches and preferably about 0.020 inches, and is advantageously from 9 to 60 inches long. Adaptors 12 and 14 each comprise means for controlling the movement of tube 16 as shown in FIGS. 2 and 3.

Referring to FIG. 2, deformable O-ring 18 is shown slidably positioned within adaptor 14 such that a space 20 exists between tube 16 and O-ring 18, the latter being in contact with screw cap 22, threaded cylinder 24 and front portion 26 of adaptor 14. In this position adaptor 14 can be slidably moved along tube 16 at will.

In FIG. 3 it is seen that when screw cap 22 is moved forward or tightened onto cylinder 24, O-ring 18 is compressed such that space 20 is eliminated and tube 16 is tightly grasped by O-ring 18, thus holding adaptor 14 in place on tube 16. In normal operation of Introreducer® 10, adaptor 14 is positioned on tube 16 such that an end thereof protrudes only part way into chamber 28 as shown in the drawings.

In the operation of Introreducer® 10, tube 16 is inserted into an occluded enteral feeding tube and pressure distributor adaptor 12 is positioned a short distance from the entrance of the enteral feeding tube with a first end of tube 16 in contact with the occlusion to be removed. At this position, screw cap 22 is tightened so tube 16 is held in place as illustrated in FIG. 3.

In a preferred embodiment, screw cap 22 is tightened only sufficiently to provide movement to tube 16 in the absence of any obstruction, thereby permitting pressure distributor adaptor 12 to slide or slip if an obstruction is met. This prevents perforating the feeding tube wall necessitating the removal and replacement of said feeding tube.

The polycarbonate tube chosen is such that the outside diameter of the tube of said Introreducer is at least about 0.002 inch less than the diameter of the occluded lumen and is preferably about 0.01 to 0.02 inch less, the Introreducer being of sufficient length to reach the occlusion that is to be removed and preferably, the end of the tube to be cleaned and cleared. Furthermore, depending on the nature of that occlusion, the Introreducer tube is chosen to have appropriate fluid injection properties. The Introreducer is then filled with the appropriate solution, for example, warm water, preferably about 100° to about 130° F. or an enzyme solution and is inserted into the occluded tube, with small amounts of the fluid being injected to assist in lubrication. When the inserted Introreducer meets an obstruction, as indicated by retrograde flow of the water or solution, the injection rate of the water or enzyme solution is increased and the Introreducer is mechanically rotated and/or oscillated, usually by hand movement employing pressure distributor adaptor 12, to facilitate the erosive force of the injected fluid. This procedure is continued until the retrograde flow of the injected fluid stops, indicating that the occlusion has been removed and the feeding tube is now clear.

In the removal of food occlusions, warm water is preferably used if the occlusion is of short duration, i.e., several hours or less. If the occlusion is of longer duration an enzyme solution such as, for example, a solution of

| a. | Lipase | — | 4,000 | — | 8,000 U.S.P. units |
| b. | Amylase | — | 20,000 | — | 40,000 U.S.P. units |
| c. | Protease | — | 25,000 | — | 50,000 U.S.P. units in warm water | at a pH of 7.0 to 8.5 is preferred. The pH may be adjusted with baking soda, e.g. ¼ teaspoon of baking soda in a total volume of 45 cc of warm water, 100°–130° F. When using enzymes, it is at times beneficial to allow the enzyme to remain in contact with the occluded material for a short time, e.g. ½ hour, before continuing to inject more solution.

To illustrate the advantageous effects of employing the apparatus and method of the present invention, a dried sample of Ensure® plus HN was placed in water at room temperature. There were no observable effects after six hours. In 12 hours the edge of the sample was dissolving. A similar experiment except for employing Adolph's tenderizer, produced some edge dissolution in six hours. The sample was still shaped and hard after 12 hours. A third experiment employing the enzyme solution described above dissolved the edge of the sample in about one hour. In three hours the sample was soft with major liquefaction. In six hours the sample was totally dissolved. In contrast to the above, employing the Introreducer of this invention and 80 cc of warm water, 100°–150° F., a hole through the sample was produced in two minutes. Employing an Introreducer having a pointed cutting end resulted in the hole being produced in less than one minute.

The invention is further illustrated by the following examples:

EXAMPLE 1

Patient Mrs. X is in need of enteral feeding for a mental and emotional disorder. She has a Dobbhoff post-pyloric feeding tube, (8 FR) placed with x-ray confirmation of position. Her tube becomes occluded after about 24 hours of feeding with Osmolite ® at 30 cc/hour. The tube can not be cleared by the nurse educator working with the nutritional support service.

Procedure:
1. A 6 FR high pressure 42 inch Introreducer having high flow properties is selected.
2. The 6 FR Introreducer is filled with warm water with a 60 cc syringe.
3. The Introreducer is inserted into the 8 FR Dobbhoff occluded tube and with irrigation it is advanced to the occlusion.
4. The warm water flows retrograde with movement of the Introreducer in and out against the occlusion with turning action.
5. The occlusion resistance becomes less. When the injected solution stops its retrograde flow, the Introreducer advanced.
6. The Introreducer is pulled.
7. The 60 cc syringe is used to inject directly in the 8 FR Dobbhoff feeding tube.
8. The Dobbhoff tube is clear, no resistance in injecting the warm water, and the tube is put back to 30 cc/hour of enteral feeding as ordered for the patient.

EXAMPLE 2

A six-year old boy with a long-term feeding problem and a permanent J-tube is having a problem with his feeding injections. This tube is placed by surgical operation and would have to be removed and replaced the same way. The parents are most concerned as they had worked with the tube for along time and had no luck in clearing the occlusion. Their doctor had also tried without success.

This tube has a tapered lumen with the small end being around 6 FR in about 9 inches from the entrance of the tube. The tube has been blocked for 72 hours with the last feeding being Pulmocare ®.

Precedure:
1. Enzyme solution is set up by pharmacy (Lipase, Amylase, Protease as above described).
2. A 17 gauge high pressure walled 9 inch long with a high fluid force orifice Introreducer is selected.
3. The enzyme solution is instilled into the Introreducer.
4. The Introreducer is inserted into the J-tube until it meets resistance.
5. The enzyme solution is then injected with a collection basin for the retrograde flow and enzyme solution at the entrance port of the feeding tube.
6. The occlusion is hard and initially can not be removed by the direct flow and moving the tube back and forth against the occlusion with turning and cutting.
7. The enzyme is left in the J-tube for 30 minutes.
8. The Introreducer is again moved back and forth after the 30 minutes with injection of additional enzyme.
9. Resistance is still high.
10. The Introreducer was removed and 60 cc of fresh warm water is instilled into the Introreducer.
11. The J-tube is irrigated with warm water for 5 minutes while applying high fluid cutting force while collecting the spent solution in the basin from the retrograde flow. This solution shows some food is being removed.
12. The enzyme solution is reinstilled in the Introreducer and injected into the J-tube and let set for 30 minutes.
13. The J-tube is tested again by trying to advance the Introreducer, this time only minimal resistance is encountered and the Introreducer can be readily advanced.
14. The Introreducer is pulled and the J-tube irrigated with 120 cc of warm water to assure a clear lumen.

What is claimed is:
1. A method for removing occlusions from tubes employed for enteral feeding which comprises inserting an inner polycarbonate tube having a first end and a second end into said occluded tube, said inner tube having pressure distributor means slidably and fixedly positioned between said first and second ends, said inner tube being positioned such that said first end is adjacent to the occlusion to be removed, said second end being adapted to supply water or enzyme solutions to said inner tube, and passing warm water or an enzyme solution through said inner tube while applying a force to the pressure distributor means and providing a rotary and/or oscillatory motion to said inner polycarbonate tube which pushes said tube against said occlusion so as to dislodge and remove said occlusion, the pressure distributor means being adjusted such that said means slide on said inner tube before a force sufficient to perforate said enteral feeding tube is reached.

* * * * *